United States Patent [19]

Godfrey

[11] 4,143,552
[45] Mar. 13, 1979

[54] COAL SEAM SENSOR

[75] Inventor: David E. Godfrey, Burnt Hills, N.Y.

[73] Assignee: General Electric Company, Schenectady, N.Y.

[21] Appl. No.: 882,412

[22] Filed: Mar. 1, 1978

[51] Int. Cl.² .......................................... G01N 29/00
[52] U.S. Cl. ........................................ 73/579; 299/1
[58] Field of Search ................ 73/579, 594, 573, 104, 73/574, 659, 517 R; 175/50; 299/1

[56] References Cited
U.S. PATENT DOCUMENTS 3,150,519 9/1964 Heimaster et al. ................ 73/104 X
3,793,627 2/1974 Darrel et al. ...................... 73/104 X Primary Examiner—Jerry W. Myracle
Attorney, Agent, or Firm—Donald R. Campbell; Joseph T. Cohen; Marvin Snyder

[57] ABSTRACT

The frequency response of the cutting tool of a coal mining machine is monitored at a resonant frequency of the cutting tool, using a vibration transducer mounted on a non-rotating support arm, to detect the difference between coal and rock or other enclosing material. The horizon control sensor maintains the mining machine within the undulating coal seam.

4 Claims, 5 Drawing Figures

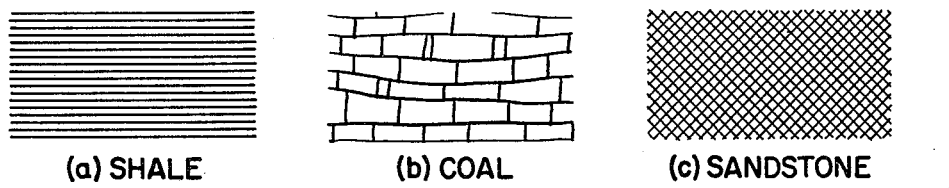
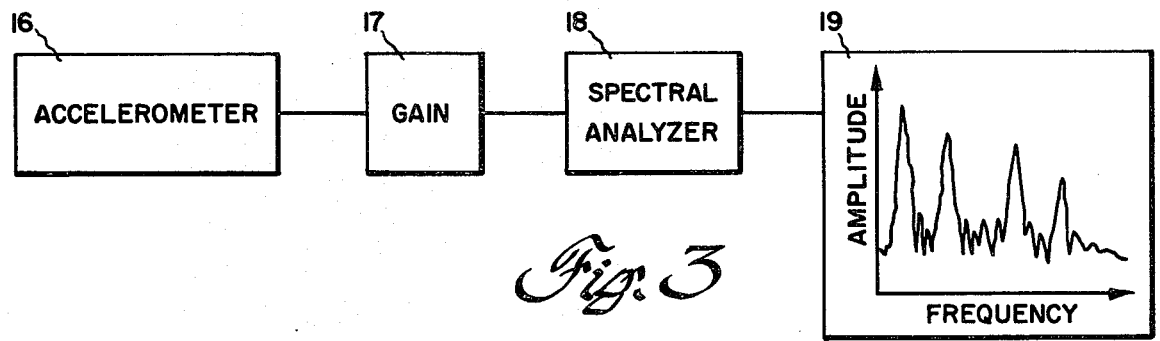
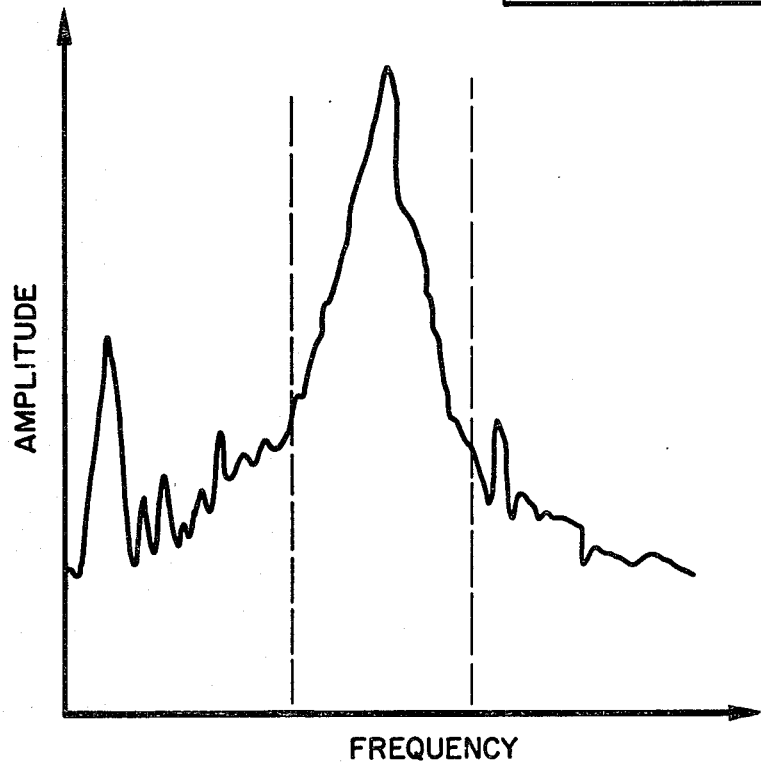
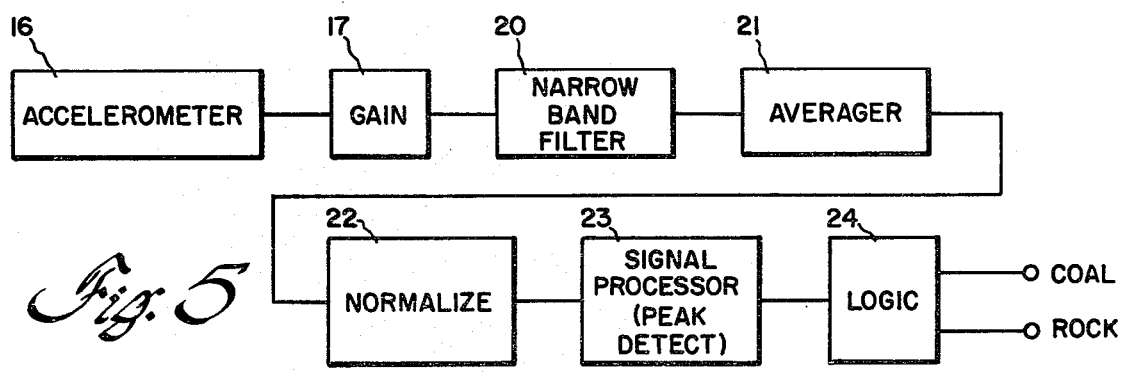

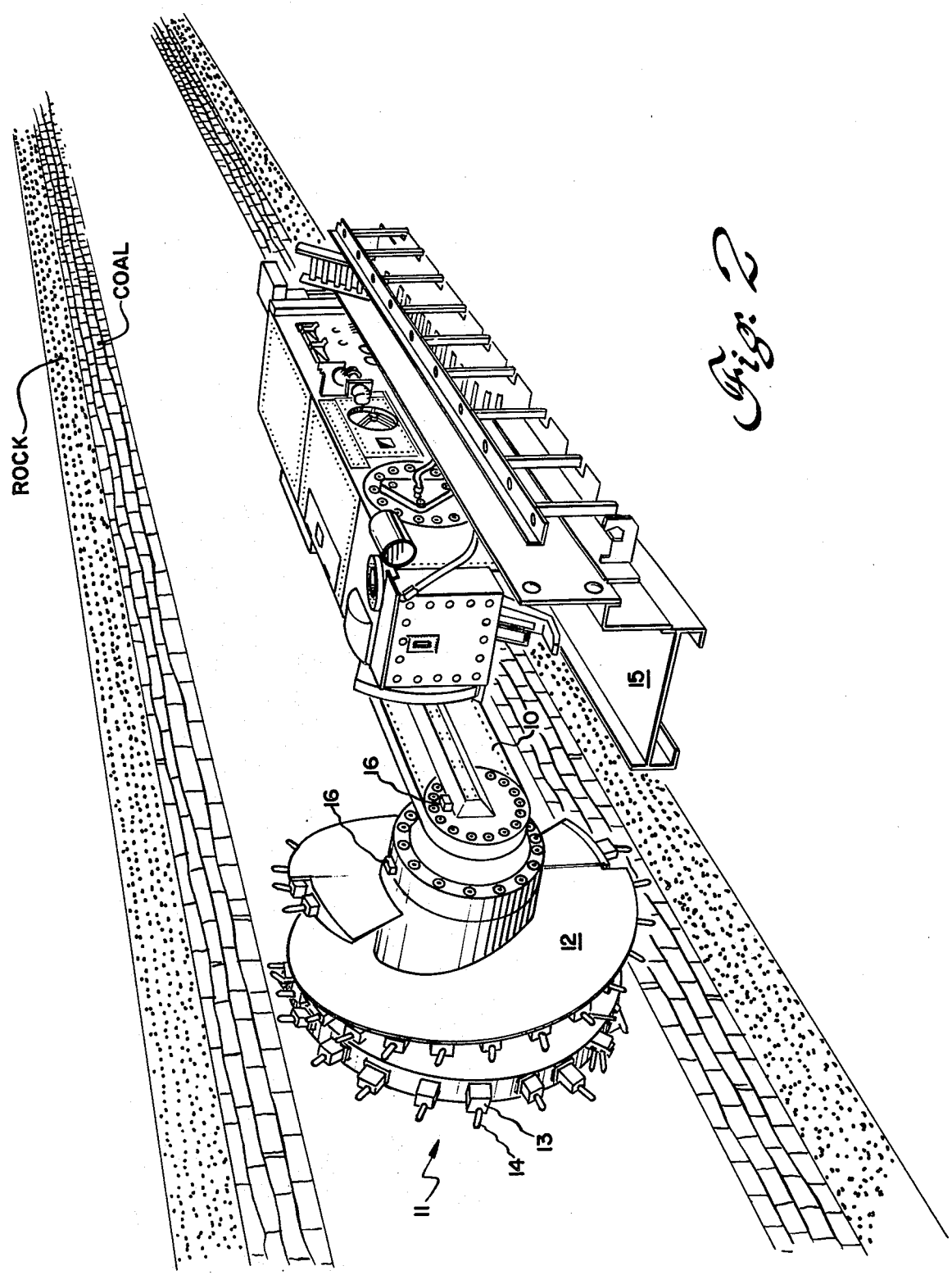

COAL SEAM SENSOR

BACKGROUND OF THE INVENTION

This invention relates to coal mining, and more particularly to an improved horizon control sensor for detecting engagement of the cutting tool of a coal mining machine with rock or other material enclosing a coal seam.

Underground coal mining is done with longwall drum shearers and continuous miners which are controlled by an operator to maintain the cutting tools in the undulating coal seam. The most critical need for increasing the productivity and safety of the underground mining of coal is an improved sensor to control the elevation of the drums on the shear loader machine of a longwall mining machine and the elevation of a continuous mining machine. Such a device would allow mining to be done at the maximum operating speed of the machine and not be slowed down by the operators, would reduce the waste material taken from the floor and ceiling while maximizing the amount of coal taken, and is the key to automated coal mining machines which will allow the operator to run the machine while located outside the hazardous face area.

Two systems for the automatic detection of the interface between coal and surrounding rock are the sensitized pick and the nucleonic sensor. The sensitized pick is a strain gage transducer and earlier attempts to develop a working device proved feasibility but it was not further developed. The nucleonic sensor relies on a gamma ray back scattering technique that measures the remaining coal thickness by reflecting gamma rays off the coal-rock interface. This system was developed into a marketable product but does not properly do the job. U.S. Pat. No. 2,944,804 to Persson discusses monitoring the vibration of the rotating cutting tool of a mining machine by accelerometers mounted on the machine to sense the higher amplitude of vibration exceeding a preset level when the cutting bit enters rock. Tool vibration amplitude differences between coal and rock are dependent on material hardness which is not a unique discriminant. Many coal fields are enclosed in material softer than rock and cannot be followed by measuring higher vibration amplitude alone. This combined with amplitude vibrations which occur due to machine movements, dull tools, and other external operations make this concept risky.

SUMMARY OF THE INVENTION

The frequency spectrum at and near a resonant frequency of the cutting tool of a coal mining machine is monitored by a vibration sensor mounted on a non-rotating support arm for the tool, and is a discriminant to differentiate the cutting of coal from the cutting of rock or other coal seam enclosing materials. The frequency response at a resonant or natural frequency is related to the response of the tool to the material as it is impacted, and the response depends not only on hardness but also on the extent of prefracturing. This latter quality is unique to coal which is prefractured as well as being softer than rock.

The horizon control sensor in an exemplary embodiment is comprised by at least one vibration transducer mounted on the support arm for sensing the broad band sonic vibrations of the cutting tool; a narrow band filter for extracting from the vibration signal the response at and near a preselected resonant frequency of the cutting tool; and a signal processor for deriving from an extracted resonant peak a discriminant for sensing the engagement of the cutting tool with the interface between coal and rock and other enclosing materials such as clay. The characteristics of the extracted signal at resonance, such as the Q and amplitude of the resonant peak, can discriminate coal from shale and limestone or from enclosing materials softer than coal. It is also necessary to normalize the vibration signal to compensate for variations in depth of cut and other machine parameters.

BRIEF DESCRIPTION OF THE DRAWINGS

FIGS. 1a–1c are cross sections of shale, coal and sandstone illustrating the material characteristics that result in different cutting tool frequency responses;

FIG. 2 is a simplified perspective view of a longwall shearer coal mining machine showing the positions of the vibration transducers;

FIG. 3 is a block diagram of equipment for testing the frequency of a single cutting bit;

FIG. 4 depicts an extracted resonant peak in a plot of amplitude vs. frequency; and FIG. 5 is a block diagram of a horizon control sensor for discriminating coal from rock and other enclosing materials.

DESCRIPTION OF THE PREFERRED EMBODIMENT

The basic concept of the horizon control sensor is to monitor the vibrations of the cutters in the frequency domain as they cut through coal and rock. An underground coal seam can also be enclosed by softer materials such as clay, but highly compacted clay approaches the hardness of rock and the following description for simplicity discusses detecting the interface between coal and rock at the periphery of the coal seam. The rotating cutting tool of a continuous miner or longwall shearer has multiple cutting bits at evenly spaced circumferential positions that individually rotate into and out of engagement with the material being cut. The cutting bit behaves like a beam that is excited by the impacts with the material during the cutting process. The response of the beam is a function of the material density and the ability of the material to get out of the way after each impact and allow the beam to vibrate in a relatively uninhibited fashion. The latter will depend on the amount of prefracturing as well as on the brittleness and friability of the material. All of these properties combined represent a distinct set of discriminants between coal and the surrounding materials. The major forcing function is provided by the cutting edge of the bit contacting the material, and the material additionally is a constraint on the vibration of the tool and its holder structure. Coal and rock are different as an exciter and especially as a constrainer, since these materials have different hardnesses and different fractures.

The major structural characteristics of shale, coal and sandstone are depicted in FIG. 1a–1c. Shale has a laminated or layered structure, and a semiconchoidal fracture is common in shale, causing it to split parallel to the bedding into thin shell-like plates or fragments. Shale is essentially clay that has been converted into rock and it is therefore high in clayey constituents. Coal has a laminated or layered structure parallel to the bedding, and is unique in that it is also prefractured perpendicular to the bedding. Coal is lower in density by 2:1 compared to its enclosing rock and is prefractured (also known as cleats) while the enclosing rock is not. Sandstone has a homogeneous composition and consists of firmly cemented sand grains. The grain size is much larger than in shale, and sandstone when fractured breaks around the grains instead of through them because the grains are ordinarily stronger than the cement.

The key to this horizon control sensor is to monitor the frequency spectrum at and near the resonant frequency of the cutting tool because it is at a resonant frequency that the differences between coal and rock are more pronounced. The mining machine will have many sources of impacts and hence many vibration signals that are not related to the cutting media. However, if the response of the vibration transducer is examined around the vibration frequencies that are associated with the cutting tool, misleading information can be eliminated. This frequency range of interest is a property of the cutting tool geometry. The characteristics of the response, such as amplitude and Q, and also the harmonics of the fundamental resonant frequency are a function of the material being cut and are the signals that are processed. Another important aspect of the sensor is that the vibration transducer is mounted on the non-rotating support arm of the mining machine, rather than on the rotating cutting tool itself. The vibration of the tool is structure-borne through the tool holder and drum to the support arm, and this technique of monitoring a moving parameter from a distance, relying on structure to transmit the information, has proven successful in a number of prior machinery diagnostic projects.

A longwall shearer mining machine (FIG. 2) has a ranging support arm 10 whose inclination or elevation can be changed and which has at its forward end a rotatable cutting tool indicated generally at 11 which is comprised of a rotating drum 12 having at its periphery a number of circumferentially spaced tool holders 13 and radially projecting cutting bits 14. The machine is movable forwardly and backwardly along haulage track 15 by a conveyor system, and the operator can control the haulage speed and depth of cut, among other things. One or more accelerometers 16 are mounted on ranging arm 10 to sense the sonic vibrations of the cutting tool. The accelerometers may be mounted in different directions, such as parallel to and transverse to the axis of the ranging arm, but this is not essential. Three accelerometers mounted orthogonally will pick up all modes of vibrations. The modes are coupled; therefore, any one sensor may be sufficient. The best choice depends on the machinery geometry and is easily determined by tapping a tool on the drum when the machine is stopped and measuring the response, seeking the position with maximum signal transfer from the tool to the sensor. The transducer consists of a piezoelectric crystal that vibrates like a spring/mass in response to the excitations at its base, and the signal voltage output is then proportional to the acceleration. The vibrations of the bit are transmitted through the structure of the tool holder and rotating drum to the ranging arm and thence to the accelerometers.

Equipment such as is shown in FIG. 3 for a laboratory test of a single cutting bit can also be used to record the frequency spectrum of a mining machine cutting tool and determine the resonant frequency or frequencies of interest. The electrical output signal of accelerometer 16 is amplified in circuit 17 and fed to a real time spectral analyzer 18 which samples the data for a controlled interval and then takes the Fourier transform and plots it on a cathode ray tube or pen recorder 19. This plot gives a relative amplitude of the frequency components averaged over the sample period of time. An ensemble of data are used representing the average of a number of samples. Examination of data for coal, sandstone, and shale showed that there were resonant peaks corresponding to the first natural frequency of the tool and its harmonics, and that the frequency response at resonance can be a reliable coal/rock interface discriminant. Major elements of difference between coal and shale or sandstone are that the resonant peaks for coal are sharper than those for sandstone and shale and that the overall signal amplitude for sandstone and shale is higher than that of coal. The amplitude, however, varies heavily relative to the depth of cut and is useful if the signal is normalized. Another major difference is that more energy is expended at high frequencies for rock and shale than for coal. Also, for single tool tests, amplitudes of the second and third harmonics continually decrease for coal but not for sandstone and shale.

These points of difference can be rationally tied to the physics of the material. The trait of the sharpness of the peaks is caused by the ability of material to break away as the impacts take place, allowing the tool to vibrate freely at its natural frequencies. For coal, which has the unique feature of being prefractured, this gives rise to sharp peaks comparable to a lightly damped system. The sandstone is more homogeneous in nature, has no prefracturing, and tends to cut a grain at a time. The response of the tool for this material is comparable to that for a heavily damped system. The peaks are not sharp but are round and spread over a broader base. In the case of shale, where the material seems to be brittle but not prefractured, as in coal, the peaks again become sharper. Visual observation shows the material does fragment more like coal, but not as easily, and gives rise to the higher frequency content of a stiffer system. Regarding the lower frequency content for coal as compared to rock, because coal is soft and prefractured, it gives way to the initial impact and will not tend to excite the higher frequencies. That is, it is a soft spring system that denotes low frequency response. For sandstone and shale, the impacting material represents a stiffer system and tends to excite the higher frequencies. Another possible discriminate not previously mentioned is a slight frequency shift of the first harmonic which is amplified at the natural frequencies of the tool. The data was evaluated for consistency and it was found that the general shape of the frequency curves was constant and repeatable, and unique for a given material.

The resonant frequencies of interest for an actual mining machine cutting tool such as that in FIG. 2 can be determined by experimentation. The cutting tool components including the bits, tool holders, and rotating drum all have resonant frequencies, and one of the cutting tool natural frequencies is selected as the coal/rock discriminant. There are many other sources of vibration as the mining machine operates, such as gears, motors, etc., and the overall vibration signal detected by the accelerometer has a large noise component. The desired vibration signal due directly to cutting, however, is accentuated and is relatively consistent at the selected resonant frequency. In the horizon control sensor, then, the portion of the overall vibration signal at and near the selected resonant frequency is extracted, as depicted in FIG. 4, and electronically processed to give an indication of coal or rock. The characteristics of the extracted vibration signal at and near the resonant peak, i.e., the amplitude and sharpness of the resonant peak (Q), are reliable discriminates for detecting engagement of the cutting tool with the interface between coal and rock.

The outline of a horizon control sensor relying on differences in vibration signal amplitude at a natural frequency is given in FIG. 5. The amplified accelerometer output signal is passed through a narrow band filter 20 and averaged over a number of cycles in an averager 21. The extracted signal is normalized, as by the use of an automatic gain control 22, to compensate for variations in amplitude caused by depth of cut and other mining machine parameters including the cutting tool rpm and the haulage speed. The normalized narrow band signal is then presented to a signal processor 23 for peak detection or average level detection. The output of the signal processor is a variable dc level with a higher magnitude for rock than for coal. One type of output display is to present the dc signal to appropriate logic 24 to turn on a green light if the drum shearer is in the coal seam and to turn on a red light if the drum shearer is out the coal seam and corrective action should be taken. In an ultimate approach, the output can be tied in a servo loop to the drum shearer control to raise and lower the drum automatically. A modification to this circuit is that a comparator and peak detector can be added, with a filter sweep control, to insure that the filter is centered around the resonant peak. This will allow for frequency changes that may occur with tool wear and wear in other cutting tool parts. It will be noted that the dc output signal from signal processor 23 has a lower magnitude than coal when the enclosing material is a type of clay softer than coal.

The best mode for the practice of the invention presently known to the inventor and a specific implementation thereof is described in a paper entitled "Mechanical Signature Analysis for Coal/Rock Interface Detection" by N. R. Kuchar and B. Darrel, presented orally to the Engineering Foundation Conference on Applications of New Signature Analysis Technology, Rindge, New Hampshire, July 1977. This paper is submitted for publication in the Conference Proceedings. The coal/rock discriminate described by Kuchar and Darrel is a spectral ratio provided by the amplitude of a resonant vibration frequency of the cutter divided by the amplitude at another normalizing, non-resonant frequency so as to produce a quantity independent of shearer operating parameters. Resonant and normalization frequencies are determined by examination of a vibration spectrum of the operating shearer, i.e., the sensor must be tuned for each specific machine.

While the invention has been particularly shown and described with reference to several preferred embodiments thereof, it will be understood by those skilled in the art that various changes in form and details may be made therein without departing from the spirit and scope of the invention.

The invention claimed is:

1. A horizon control sensor for a coal mining machine having at least one support arm on which is mounted a rotatable cutting tool, comprising:
    at least one vibration transducer mounted on the support arm to sense the sonic vibrations of the rotatable cutting tool and generate an electrical signal representative thereof,
    filter means for extracting from said vibration signal at least one narrow band of frequencies at and near a preselected resonant frequency of the cutting tool, and
    signal processing means for deriving from an extracted resonant peak a discriminant for distinguishing engagement of the cutting tool with the interface between coal and rock and other coal seam enclosing materials.

2. The horizon control sensor of claim 1 wherein said signal processing means derives a discriminant dependent on the amplitude and shape of the extracted vibration signal at and near the resonant peak determined by the damping characteristic and hardness of the material.

3. The horizon control sensor of claim 1 or claim 2 further including means for normalizing the extracted vibration signal to compensate for amplitude variations caused by variations in depth of cut and other mining machine parameters.

4. The horizon control sensor of claim 1 further including means for generating an output signal indicative of coal and of rock and other enclosing materials and for visually displaying said output signal.

* * * * *